US00PP08433P

United States Patent [19]

Zaiger et al.

[11] Patent Number: Plant 8,433

[45] Date of Patent: Oct. 26, 1993

[54] APRICOT TREE "GOLD BRINK"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 997,528

[22] Filed: Dec. 28, 1992

[51] Int. Cl.[5] ..... A01H 5/00

[52] U.S. Cl. ..... Plt./39

[58] Field of Search ..... Plt. 39

[56] References Cited

U.S. PATENT DOCUMENTS

PP. 5,138 11/1983 Zaiger ..... Plt. 39

*Primary Examiner*—James R. Feyrer

[57] ABSTRACT

Our new and distinct variety of apricot tree has the following unique combination of features that are outstanding in a new variety:

1. Heavy and regular production.
2. Fruit with good flavor and eating quality.
3. Fruit with firm flesh, good handling and shipping quality.
4. Vigorous, semi-spreading growth.
5. Early maturity of large size fruit.

1 Drawing Sheet

ORIGIN OF THE VARIETY

The present new variety of apricot tree was originated by us in our experimental orchard located near Modesto, Calif. as a first generation seedling from a cross between a selected seedling and King Cot (nonpatented). The seedling selection which was the female parent originated from open pollinated Flaming Gold seed grown by us. We grew and maintained a large group of these first generation seedlings under careful observation and one seedling having especially desirable fruit characteristics, which is the present variety, was selected for asexually reproduction and commercialization.

ASEXUAL REPRODUCTION OF THE VARIETY

The new and distinct variety of apricot tree was asexually reproduced by budding, as performed by us in our experimental orchard located near Modesto, Calif. and shows that all characteristics are established and transmitted through succeeding propagations and run true to the original tree in all respects.

SUMMARY OF THE VARIETY

The herein new variety of apricot tree is of large size, vigorous, semi-spreading growth and a productive and regular bearer of large, firm, yellow flesh, freestone fruit with good flavor and eating quality. The fruit is further characterized by being relative uniform in size throughout the tree, having the ability to ship to long distance markets and in comparison to Flaming Gold Apricot (U.S. Plant Pat. No. 2,822) the tree has heavier fruit production, and the fruit matures approximately 9 days earlier.

BRIEF DESCRIPTION OF THE PHOTOGRAPHS

The accompanying photographic reproductions in color show typical specimens of the foliage and fruit of the present new variety of apricot tree. The illustrations show the upper and lower surface of the leaves, the exterior and a sectional view of the fruit divided in the suture plane to show flesh coloration, pit cavity and a stone remaining in place. The photographic illustrations were taken shortly after being picked at maturity (firm ripe) and the colors are as nearly true as is reasonably possible in a color representation of this type.

DESCRIPTIONS OF THE VARIETY

The following is a detailed botanical description of the new and distinct variety of apricot tree, its flowers, foliage and fruit based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Semi-spreading.
- *Density.*—Medium dense.
- *Shape.*—Usually pruned to vase shape.
- *Production.*—Productive.
- *Bearer.*—Regular.

Trunk:
- *Size.*—Large.
- *Texture.*—Shaggy.
- *Color.*—Brown to leather brown (6-E-4) to (6-E-6).

Branches:
- *Size.*—Medium.
- *Texture.*—Medium rough.
- *Lenticels.*—Numerous. Large size.
- *Color.*—New growth — reddish brown. Old growth — light brown to brown.

Leaves:
- *Size.*—Large. Average length — 5" to 5½". Average width — 2¾" to 2¼".
- *Form.*—Ovate.
- *Thickness.*—Medium.
- *Texture.*—Smooth.
- *Margin.*—Serrate.
- *Petiole.*—Average length — 2". Medium thickness.

*Glands.*—Number varies from 0 to 4. Average number 2. Majority located on upper portion of petiole, few on base of leaf blade. Globose. Small size.

*Color.*—Upper surface — green (27-F-4) to (27-F-6). Lower surface — grayish green to green (27-E-3) to (27-E-5).

Flower buds:

*Size.*—Medium to large.

*Length.*—Medium.

*Form.*—Plump.

Flowers:

*Size.*—Large.

*Blooming period.*—Date of first bloom Feb. 24, 1990. Date of full bloom Mar. 1, 1990. Varies slightly with climatic conditions.

*Pollen.*—Present.

*Color.*—Light pink.

Fruit:

*Maturity when described.*—Firm ripe.

*Date of first picking.*—May 23, 1990.

*Date of last picking.*—May 28, 1990.

*Size.*—Large. Average diameter axially — 2" to $2\frac{3}{8}$". Average diameter in suture plane — 2" to $2\frac{1}{8}$". Average diameter measured at right angles to suture plane — $1\frac{7}{8}$" to 2".

*Form.*—Nearly globose, slightly elongated in suture plane and slightly flattened at the base.

*Suture.*—Pronounced, extends from base to apex.

*Ventral surface.*—Suture line slightly wider than normal, varies from rounded to slightly lipped.

*Apex.*—Usually slightly retuse — varies from slightly retuse to slight tip.

*Base.*—Retuse.

*Cavity.*—Rounded to slightly elongated in suture plane. Average depth — $\frac{1}{4}$" to 3/16". Average breadth — $\frac{1}{2}$" to $\frac{5}{8}$".

Flesh:

*Ripens.*—Evenly.

*Texture.*—Firm.

*Amygdalin.*—Undetected.

*Juice.*—Moderate.

*Aroma.*—Moderate.

*Flavor.*—Good — mild, predominately apricot.

*Eating quality.*—Good.

*Color.*—Yellow to light orange (5-A-5) to (5-A-6).

Skin:

*Thickness.*—Medium.

*Texture.*—Medium — tenacious to flesh.

*Tendency to crack,.*—Very slight.

*Down.*—Scant very short.

*Color.*—Yellow to light orange (5-A-4) to (5-A-5).

Stone:

*Type.*—Freestone.

*Size.*—Medium. Average length — $1\frac{1}{8}$" to 1 3/16". Average breadth — $\frac{3}{4}$" to $\frac{7}{8}$". Average thickness — $\frac{1}{2}$" to $\frac{5}{8}$".

*Base.*—Usually straight — varies from straight to rounded.

*Apex.*—Usually acuminate — varies from acuminate to nearly rounded.

*Sides.*—Equal to unequal.

*Ridges.*—Slight ridges extending across surface of the stone on both sides of suture plane.

*Surface.*—Pitted throughout.

*Tendency to split.*—None.

*Color.*—Light brown to brown (6-D-6) to (6-D-7).

Use: Dessert.

*Market.*—Local and long distance.

Keeping quality: Good.

Shipping quality: Good.

The present new variety of apricot tree, its flowers, foliage and fruit herein described may vary in slight detail due to climatic, soil conditions and cultural practices under which the variety may be grown; the present description is that of the variety grown under the ecological conditions prevailing near Modesto, Calif.

We claim:

1. A new and distinct variety of apricot tree, substantially as illustrated and described, characterized by its large size, vigorous, semi-spreading growth and a productive and regular bearer of large, yellow flesh, freestone fruit; the fruit is further characterized by having firm flesh with good flavor and eating quality, having good handling and shipping quality and in comparison to Flaming Gold Apricot (U.S. Plant Pat. No. 2,822) it has heavier fruit production and the fruit ripens approximately 9 days earlier.

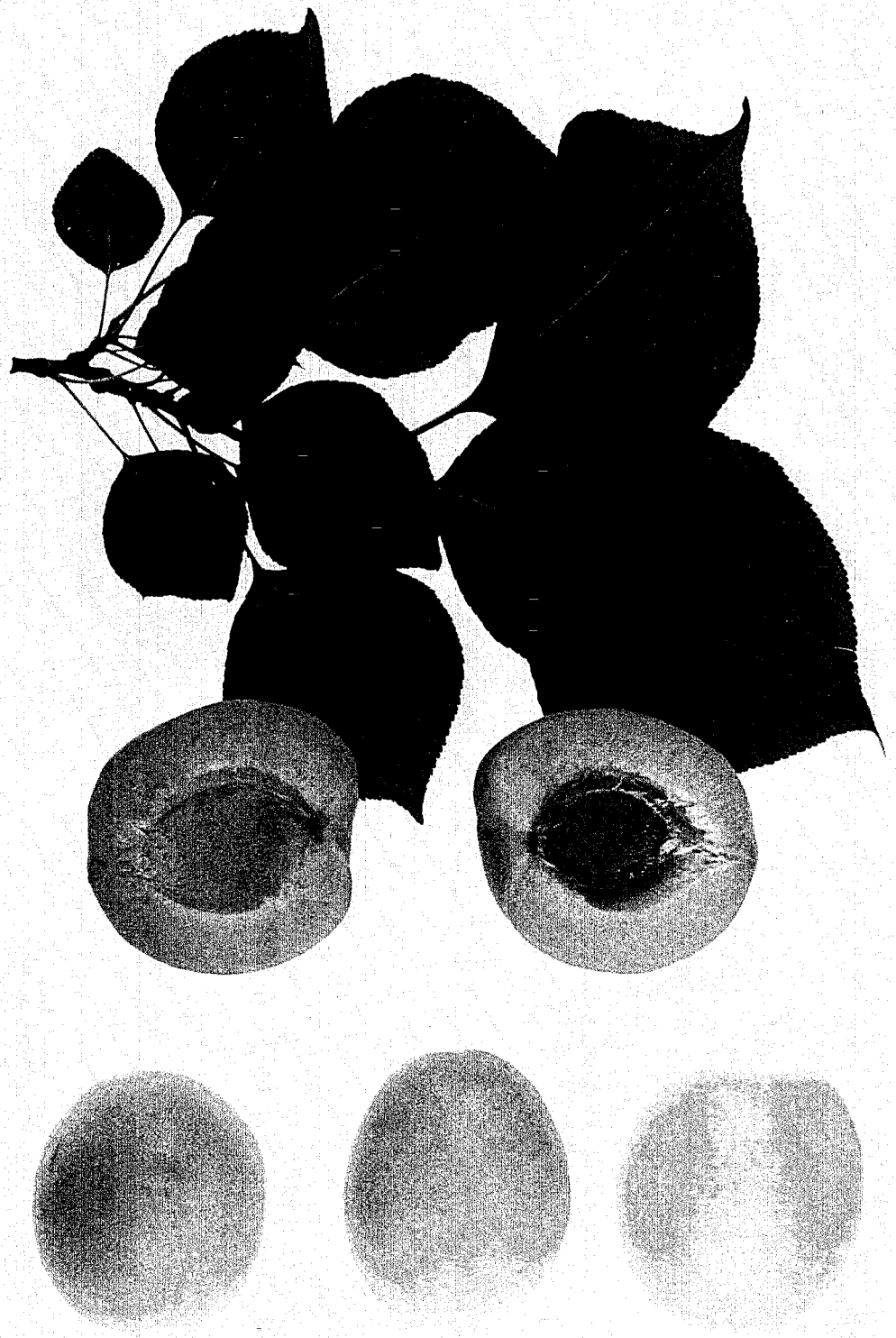

* * * * *